United States Patent [19]

Siegle et al.

[11] 3,968,232
[45] July 6, 1976

[54] N-METHYL-N-ALKOXYCARBONYLSULPHENYL-CARBAMATES

[75] Inventors: Peter Siegle, Cologne; Engelbert Kühle, Bergisch-Gladbach; Ingeborg Hammann, Cologne; Wolfgang Behrenz, Overath-Steinenbruck, all of Germany

[73] Assignee: Bayer Aktiengesellschaft, Leverkusen, Germany

[22] Filed: Oct. 29, 1974

[21] Appl. No.: 518,837

[30] Foreign Application Priority Data
Nov. 20, 1973 Germany............................ 2357930

[52] U.S. Cl............................ 424/277; 260/327 M; 260/340.7; 260/340.9; 260/455 A; 260/455 B; 260/465 E; 260/465.5 R; 260/566 D; 424/278; 424/300; 424/301
[51] Int. Cl.²........................................... A01N 9/12
[58] Field of Search......... 260/327 M, 340.7, 340.9, 260/455 B, 455 A; 424/277, 278, 300, 301

[56] References Cited
UNITED STATES PATENTS

| | | | |
|---|---|---|---|
| 3,819,649 | 6/1974 | Zumach et al. | 260/327 M |
| 3,829,437 | 8/1974 | Zumach et al. | 260/327 M |

OTHER PUBLICATIONS
Chemical Abstracts, 73:25151v, (1970), Kohn et al.

*Primary Examiner*—Sherman D. Winters
*Attorney, Agent, or Firm*—Burgess, Dinklage & Sprung

[57] ABSTRACT

N-methyl-N-alkoxycarbonylsulphenyl-carbamates of the formula

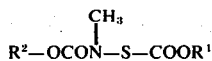

in which
R¹ is $C_{1-6}$ alkyl, and
R² is phenyl; naphthyl; indanyl; phenyl, naphthyl or indanyl substituted by trihalomethyl, halogen, nitro, nitrile, dioxanyl, dioxolanyl, methyl-dioxanyl, methyl-dioxolanyl, alkyl, cycloalkyl, alkenyl, alkynyl, alkoxy, dialkoxymethyl, alkenoxy, alkynoxy, alkylmercapto, alkenylmercapto, alkynylmercapto or dialkylamino, with up to 6 carbon atoms in each alkyl, alkenyl or alkynyl group; a radical of the formula

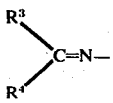

in which
R³ and R⁴ are each alkyl, alkylthio, nitrile or phenyl; or

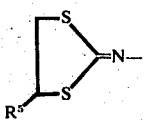

in which
R⁵ is hydrogen or $C_{1-6}$ alkyl, which possess insecticidal, acaricidal, fungicidal, nematocidal and bactericidal properties.

10 Claims, No Drawings

N-METHYL-N-ALKOXYCARBONYLSULPHENYL-CARBAMATES

The present invention relates to and has for its objects the provision of particular new N-methyl-N-alkoxycarbonylsulphenyl-carbamates, i.e. N-methyl-N-alkoxycarbonylsulphenyl-phenyl-, -naphthyl-, indanyl- or ketoxime-carbamates, which possess insecticidal, acaricidal, fungicidal, nematocidal and bactericidal properties, active compositions in the form of mixtures of such compounds with solid and liquid dispersible carrier vehicles, and methods for producing such compounds and for using such compounds in a new way especially for combating pests, e.g. insects, acarids, fungi, nematodes and bacteria, with other and further objects becoming apparent from a study of the within specification and accompanying examples.

It has been disclosed in German Published Specification DOS No. 1,949,234 that N-substituted arylcarbamates exhibit insecticidal properties. However, the disadvantages of these compounds is their low activity, above all if low concentrations are used, and their relatively high toxicity to warm-blooded animals.

The present invention provides N-sulphenylated compounds of the general formula

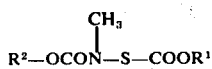

in which
R$^1$ is C$_{1-6}$ alkyl, and
R$^2$ is phenyl; naphthyl; indanyl; phenyl, naphthyl or indanyl substituted by trihalomethyl, halogen, nitro, nitrile, dioxanyl, dioxolanyl, methyl-dioxanyl, methyl-dioxolanyl, alkyl, cycloalkyl, alkenyl, alkynyl, alkoxy, dialkoxymethyl, alkenoxy, alkynoxy, alkylmercapto, alkenylmercapto, alkynylmercapto or dialkylamino, with up to 6 carbon atoms in each alkyl, alkenyl or alkynyl group; a radical of the formula

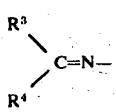

in which
R$^3$ and R$^4$ are each alkyl, alkylthio, nitrile or phenyl; or

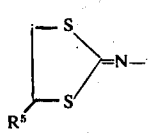

in which
R$^5$ is hydrogen or C$_{1-6}$ alkyl.

Preferably, R$^1$ is straight-chain or branched C$_{1-4}$ alkyl, especially methyl and isopropyl. Preferably R$^2$ is phenyl which can be monosubstituted or poly-substituted by straight-chain or branched alkyl with 1 to 6 carbon atoms, cyclopentyl, cyclohexyl, halogen (especially fluorine, chlorine or bromine), nitro, nitrile, dioxanyl and dioxolanyl (the two latter can each be methyl-substituted), or by alkenyl, alkynyl, alkoxy, alkenoxy, alkynoxy or alkylmercapto with up to 6 carbon atoms, or by dialkylamino with up to 6 carbon atoms in each alkyl moiety, or by trihalomethyl (especially trifluoromethyl); or R$^2$ is naphthyl or indanyl which can be monosubstituted or polysubstituted by methyl; or R$^2$ is a radical of the formula

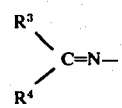

in which R$^3$ and R$^4$ are each straight-chain or branched alkyl or thioalkyl with 1 to 6 carbon atoms, nitrile or phenyl; or

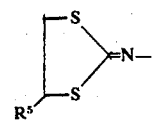

in which R$^5$ is hydrogen or methyl.

It is distinctly surprising that the compounds according to the invention have a greater insecticidal and acaricidal action than previously known commercially available carbamates of analogous action.

Furthermore, the N-sulphenylated carbamates according to the invention are far less toxic to warm-blooded animals than the corresponding unsubstituted carbamates. In addition, the compounds according to the invention are better tolerated by the skin than are known trihalomethylsulphenylated carbamic acid esters. The compounds according to the invention thus represented an enrichment of the art.

The invention also provides a process for the production of a compound of the formula (I) in which
a. a substituted carbamic acid fluoride of the general formula

in which
R$^1$ has the abovementioned meaning is reacted with a compound of the general formula

in which
R$^2$ has the abovementioned meaning, optionally in the presnce of a diluent and of an acid-binding agent, or the compound (III) is used in the form of a salt; or
b. a sulphene-chloride of the general formula

in which
R$^1$ has the abovementioned meaning is reacted with a carbamate of the general formula

in which

R² has the abovementioned meaning, optionally in the presence of a diluent and optionally in the presence of an acid-binding agent.

When N-methyl-N-methoxycarbonylsulphenyl-carbamic acid fluoride and 2-isopropoxyphenol are used as starting materials, the course of the reaction can be represented by the following equation:

OC₃H₇ⁱ attached to phenol (IIIa) + F—C(=O)—N(CH₃)—SCOOCH₃ (IIa) → phenyl-OC₃H₇ⁱ, OCON(CH₃)—S—COOCH₃ (VI) (4)

When using 2-isopropoxyphenyl-N-methyl-carbamate and methoxy-carbonylsulphene-chloride, the course of the reaction can be represented by the following equation:

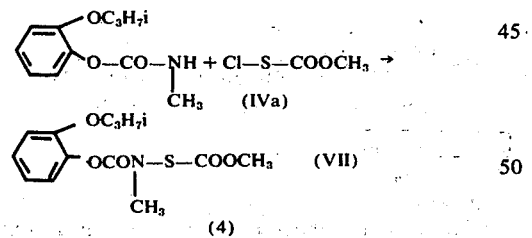

(Va) O—CO—NH(CH₃) + Cl—S—COOCH₃ (IVa) → OCON(CH₃)—S—COOCH₃ (VII) (4)

The starting materials used to prepare the compounds according to the invention are in some cases known, or can be obtained analogously to known processes. Thus, the alkoxycarbonylsulphene-chlorides of the formula (IV) are prepared according to the process of German Published Specification DOS No. 1,568,632.

The substituted carbamic acid fluorides of the formula (II) are new but can be prepared analogously to the process described in Example 7 hereinbelow, by reacting N-methylcarbamic acid fluoride with the corresponding alkoxy-carbonylsulphenyl chloride.

The preparation of the hydroxyaryl compounds of the formula (III) is known. The cyclic oximes are prepared according to the process of U.S. Pat. No. 3,183,148.

The aliphatic α-cyano-aldoximes which serve as starting materials for some of the active compounds according to the invention may be prepared by a new process comprising reacting carboxylic acid anilides with thionyl chloride, reacting the resulting α-chloroaldoximes with sodium cyanide and then saponifying the product with hydroxylamine hydro-chloride, viz.:

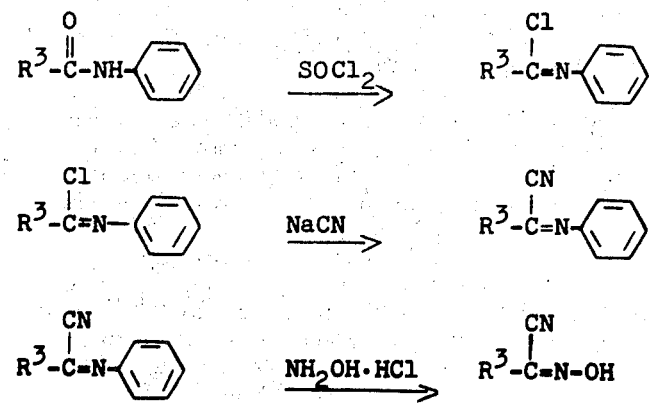

In this case, R³ preferably represents straight-chain or branched alkyl with 1 to 6 carbon atoms, especially tert.-butyl.

The carbamates of the formula (V) may be prepared according to known processes by reaction of the hydroxy compounds of the formula (III) with methyl isocyanate or with phosgene and methylamine.

All inert organic solvents can be used as diluents in the reactions mentioned. They include ethers, such as diethyl ether, dioxane and tetrahydrofuran, hydrocarbons such as benzene and chlorinated hydrocarbons such as chloroform and chlorobenzene. A tertiary base, such as triethylamine, is preferably added to the reaction mixture to bind the hydrogen halide liberated during the reaction. If desired, the alkali metal salts of the compound of the formula (III) can be used as starting material. Alternatively, all customary acid-binding agents can be used to bind the hydrogen halide formed during the reaction, for example alkali metal carbonates and alkaline earth metal carbonates, as well as alcoholates such as alkali metal methylates or alkali metal ethylates, and amines.

The reaction temperatures can be varied within a wide range; in general, the reaction is carried out at 0° to 100°C, preferably about 20°–40°C.

In carrying out the process according to the invention, the starting compounds may be employed in equimolar amounts. An excess of one or other starting compound is of no disadvantage but also does not produce any significant increase in the yield of the compounds according to the invention.

The following may be mentioned as examples of particularly active representatives of the active compounds according to the invention: N-methyl-N-methoxycarbonyl-sulphenylphenylcarbamate, N-methyl-N-methoxycarbonylsulphenyl-2-isopropylphenylcarbamate, N-methyl-N-methoxy-carbonylsulphenyl-3-isopropylphenylcarbamate, N-mthyl-N-methoxycarbonylsulphenyl-2-isopropoxyphenylcarbamate, N-methyl-N-methoxycarbonylsulphenyl-2-chlorophenylcarbamate, -3-chlorophenylcarbamate and -4-chlorophenylcarbamate, N-methyl-N-methoxycarbonylsulphenyl-3,5-dimethyl-4-methyl-mercaptophenylcarbamate, N-methyl-N-methoxycarbonylsulphenyl-3-methyl-4-dimethylaminophenylcarbamate, N-methyl-N-methoxy-carbonylsulphenyl-2-cyclopentylphenylcarbamate, N-methyl-N-methoxycarbonylsulphenyl-2-dioxolanylphenylcarbamate, N-methyl-N-methoxycarbonylsulphenyl-2-dioxanylphenylcarbamate, N-methyl-N-methoxycarbonylsulphenyl-4-methylphenylcarbamate, N-methyl-N-methoxycarbonylsulphenyl-2methoxy-4-methylphenyl-carbamate, N-methyl-N-methoxycarbonylsulphenyl-4-trifluoro-methylphenylcarbamate, N-methyl-N-methoxycarbonylsulphenyl-4-nitrophenylcarbamate, N-methyl-N-methoxycarbonylsulphenyl-2-allyloxyphenylcarbamate, N-methyl-N-methoxycarbonylsulphenyl-2-methallylphenylcarbamate, N-methyl-N-methoxycarbonyl-sulphenyl-2-propargyloxyphenylcarbamate, N-methyl-N-methoxycarbonylsulphenyl-1-naphthylcarbamate, N-methyl-N-methoxy-carbonylsulphenyl-4-methylmercaptophenylcarbamate, N-methyl-N-methoxycarbonylsulphenyl-4-cyanophenylcarbamate, N-methyl-N-methoxycarbonylsulphenyl-2-isopropylmercaptophenylcarbamate, N-methyl-N-methoxycarbonylsulphenyl-3-dimethylaminophenyl-carbamate, N-methyl-N-methoxycarbonylsulphenyl-4-(1,1-dimethylindanyl)-carbamate, N-methyl-N-methoxycarbonyl-sulphenyl- 1,3-dithiolan-2-oximo-carbamate, N-methyl-N-methoxycarbonylsulphenyl-4-methyl-1,3-dithiolan-2-oximo- carbamate, N-methyl-N-methoxycarbonylsulphonyl-α-cyano-benzaldoximo-carbamate, N-methyl-N-methoxycarabonylsulphenyl-α-cyano-propionaldoximo-carbamate, N-methyl-N-methoxy-carbonylsulphenyl-α-cyano-β-methylpropionaldoximo-carbamate, N-methyl-N-methoxycarbonylsulphenyl-α-cyano-β,β-dimethylpropionaldoximo-carbamate, N-methyl-N-methoxycarbonylsulphenyl-α-methylthioacetaldoximo-carbamate and N-methyl-N-methoxycarbonylsulphenyl-β-methyl-β-methylthiopropionald-oximo-carbamate.

As already mentioned, the new N-sulphenylated N-methylcarbamic acid esters are distinguished by an outstanding insecticidal and acaricidal activity against sucking and biting insects and mites and against hygiene pests and pests of stored products. Furthermore, some of the active compounds according to the invention possess a fungicidal, nematocidal, soil-insecticidal and microbicidal action.

The pests combatted by the novel compounds include sucking insects, biting insects, diptera and mites.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnium prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles, (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = Acanthoscelides obtectus), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the sawtoothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acari*) there are classed, in particular, the spider mites (*Tetranychidae*) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the novel compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulphoxides (e.g. dimethyl sulphoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulphates, alkyl sulphonates, aryl sulphonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, fungicides, nematocides and bactericides, or rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, fungi, nematodes and bacteria, and more particularly methods of combating insects and acarids, which comprises applying to at least one of correspondingly (a) such insects, (b) such acarids, (c) such fungi, (d) such nematodes, (e) such bacteria, and (f) the corresponding habitat thereof, i.e. the locus to be protected, e.g. to a growing crop, to an area where a crop is to be grown or to a domestic animal, a correspondingly combative or toxic amount, i.e. an insecticidally, acaricidally, fungicidally, nematocidally, or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae had been killed whereas 0% means that none of the beetle larvae had been killed.

The active compounds, the concentrations of the active compounds, the evaluation times and the results can be seen from Table 1:

EXAMPLE 2

Myzus test (contact action)

Solvent: 3 parts by weight of dimethylformamide.
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids weree killed whereas 0% means that none of the aphids were killed.

Table 1

(Insects which damage plants)
*Phaedon larvae* test

| Active compounds | Active compound concentration in % by weight | Degree of destruction in % after 3 days |
|---|---|---|
| 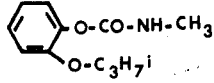 (known) (A) | 0.1<br>0.01 | 100<br>0 |
| 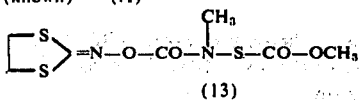 (13) | 0.1<br>0.01 | 100<br>90 |
| 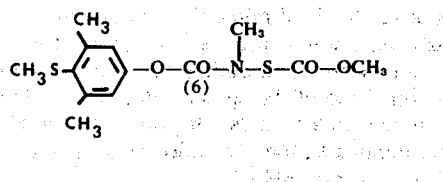 (6) | 0.1<br>0.01 | 100<br>100 |
| 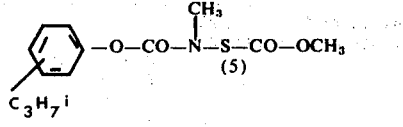 (5) | 0.1<br>0.01<br>0.01 | 100<br>100<br>100 |
| 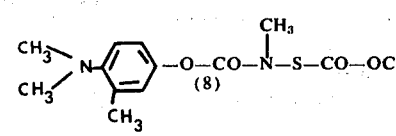 (8) | 0.1<br>0.01 | 100<br>100 |
| 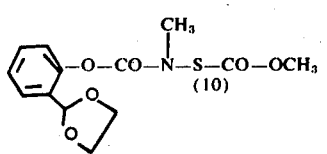 (10) | 0.1<br>0.01 | 100<br>95 |

The active compounds, the concentrations of the active compounds, the evaluation times and the results can be seen from Table 2:

Bean plants (*Phaseolus vulgaris*), which had a height of approximately 10–30 cm, were sprayed with the preparation of the active compound until dripping wet.

Table 2

(Insects which damage plants)
*Myzus* test

| Active compounds | Active compound concentration in % by weight | Degree of destruction in % after 1 day |
|---|---|---|
| 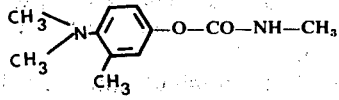 (known) (B) | 0.1<br>0.01 | 98<br>20 |
| CH₃S—C(CH₃)=N—O—CO—N(CH₃)—S—CO—OCH₃ (9) | 0.1<br>0.01 | 100<br>95 |
| 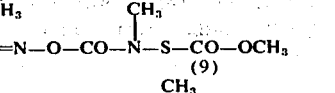 (2) | 0.1<br>0.01 | 100<br>100 |
| 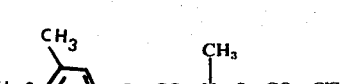 (6) | 0.1<br>0.01 | 100<br>100 |

EXAMPLE 3

Tetranychus test (resistant)

Solvent: 3 parts by weight of dimethylformamide.
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

These bean plants were heavily infested with the common or two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from Table 3:

Table 3

(Mites which damage plants)
*Tetranychus* test (resistant)

| Active compounds | Active compound concentration in % by weight | Degree of destruction in % after 2 days |
|---|---|---|
| 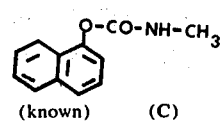 (known) (C) | 0.1 | 0 |
| 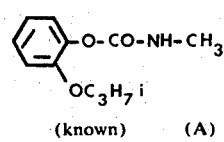 (known) (A) | 0.1 | 0 |

Table 3-continued (Mites which damage plants)
*Tetranychus* test (resistant)

| Active compounds | Active compound concentration in % by weight | Degree of destruction in % after 2 days |
|---|---|---|
| S>=N—O—CO—N(CH₃)—S—CO—OCH₃ (2) | 0.1 | 85 |
| (CH₃)(CH₃S)(CH₃)C₆H₂—O—CO—N(CH₃)—S—CO—OCH₃ (6) | 0.1 | 100 |

EXAMPLE 4

The active compounds, the nature of the substrate, and the results, can be seen from Table 4:

Table 4

| Active compounds | Residual test<br>Test insects: *Aedes aegypti*<br>Test substrate: limed clay | Destruction of the test insects in % — Age of the residual coatings in weeks |  |  |
|---|---|---|---|---|
|  |  | 1 | 2 | 3 |
| (known) (A) o-OC₃H⁷ⁱ phenyl O-CO-NHCH₃ |  |  | 8 hrs = 30% | 8 hrs = 0% |
| C₃H₇ⁱ phenyl —OCO—N(CH₃)—S—COOCH₃ (5) |  | 100 | 100 | 100 |

Residual test

Test insects: *Aedes aegypti*

Wettable powder base consisting of: 3% sodium diisobutylnaphthalene-1-sulphonate 6% sulphite waste liquor, partially condensed with aniline 40% highly dispersed silicic acid (containing calcium oxide) 51% colloidal kaolin To produce a suitable preparation of the active compound, 1 part by weight of the active compound was intimately mixed with 9 parts by weight of the wettable powder base. The spray powder thus obtained was suspended in 90 parts of water.

The suspension of the active compound was sprayed, in an amount of 1 g of the active compound per m², on to a substrate.

The sprayed coatings were, at specific intervals of time, tested for their biological activity.

For this purpose, the test insects were placed on the treated substrate. There was put over the test insects a squat cylinder closed at its upper end with a wire mesh in order to prevent the insects from escaping. After the animals had spent 8 hours on the substrate, the destruction of the test insects was determined as a percentage.

EXAMPLE 5

Preparation of N-methyl-N-methoxy-carbonylsulphenyl-phenylcarbamate

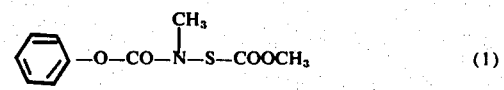

(1)

15 g (0.1 mole) of N-methyl-phenylcarbamate were dissolved in 100 ml of anhydrous toluene. 12.6 g (0.1 mole) of methoxycarbonylsulphenylchloride dissolved in 20 ml of anhydrous toluene and 10.5 g (0.1 mole) of triethylamine dissolved in 20 ml of anhydrous toluene were simultaneously added dropwise, at room temperature.

The reaction was strongly exothermic and the temperature was kept below 40°C by cooling. After completion of the reaction, the mixture was stirred for a further 2 hours at room temperature. The triethylamine hydrochloride was then filtered off, the filtrate was twice washed with water and dried with Na₂SO₄ and the solvent was then distilled off. 13 g (55% yield) of N-methyl-N-methoxy-carbonylsulphenyl-phenylcarbamate of boiling point $_{0.2}$ = 130°–140°C were obtained.

The following compound was prepared analogously:

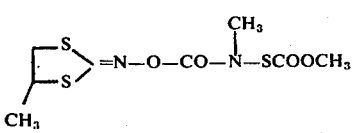   (2)

$n_D^{20}$ = 1.5644.

EXAMPLE 6

Instead of methoxycarbonylsulphenylchloride, isopropoxycarbonylsulphenylchloride was used as the starting material, and the following compound was obtained analogously to Example 5.

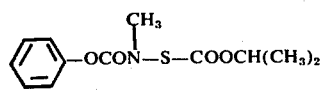   (3)

Boiling point $_{0.08}$ = 120°–125°C

EXAMPLE 7 a. Process for the preparation of the N-methyl-N-methoxycarbonylsulphenyl-carbamic acid fluoride used as a starting material 117 g (1.5 moles) of N-methylcarbamic acid fluoride and 189 g (1.5 moles) of methoxycarbonylsulphenyl chloride were dissolved in 1,000 ml of petroleum ether. 155 g (1.5 moles) of triethylamine were added dropwise with vigorous stirring; in the course thereof, the temperature was kept below 40°C.

The mixture was stirred for two hours at 30°C, the triethylamine hydrochloride produced was then filtered off, the solvent was distilled off and the residue was subjected to vacuum distillation. 116 g (47% yield) of N-methyl-N-methoxycarbonylsulphenyl-carbamic acid fluoride of boiling point $_{15}$ + 96°–99°C were obtained.

The following was prepared analogously:

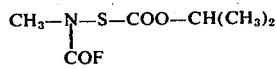

Boiling point $_{16}$ = 105°–107°C b. Preparation of N-methyl-N-methoxycarbonylsulphenyl-2-isopropoxyphenylcarbamate

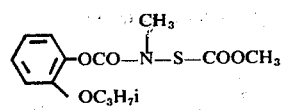   (4)

16.7 g (0.1 mole) of N-methyl-N-methoxycarbonylsulphenyl-carbamic acid fluoride and 15.6 g (0.1 mole) of 2-isopropoxyphenol were dissolved in 200 ml of toluene at room temperature. After dropwise addition of 10.5 g (0.1 mole) of triethylamine, the mixture was stirred for a further 2 hours at 30°C.

The triethylamine hydrofluoride produced was then filtered off and the filtrate was washed repeatedly with water. It was then dried over Na$_2$SO$_4$ and the solvent was distilled off. The residue was subjected to vacuum distillation. 15 g (50% yield) of N-methyl-N-methoxycarbonylsulphenyl-2-isopropoxyphenylcarbamate of boiling point $_{0.18}$ = 145°–150°C were obtained.

The following compounds were obtained analogously:

meta:para = 65:35

Oil $n_D^{20}$ = 1.5213   (5)

Oil $n_D^{20}$ = 1.5583   (6)

Oil $n_D^{20}$ = 1.5910   (7)

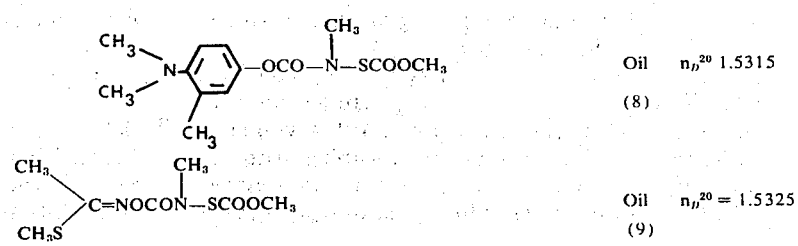

Oil $n_D^{20}$ 1.5315   (8)

Oil $n_D^{20}$ = 1.5325   (9)

-continued

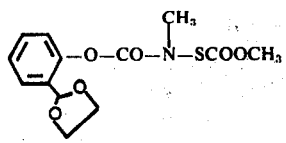

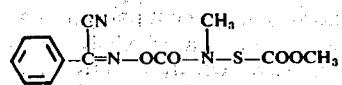

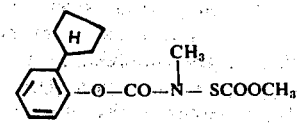

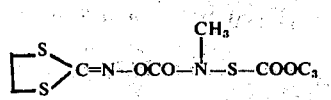

It will be appreciated that the instant specification and examples are set forth by way of illustration and not limitation, and that various modifications and changes may be made without departing from the spirit and scope of the present invention.

What is claimed is:

1. An N-methyl-N-alkoxycarbonylsulphenyl-carbamate of the formula $$R^2-OCON-S-COOR^1$$
$$\phantom{R^2-OCON}|$$
$$\phantom{R^2-OCON-S}CH_3$$

in which
R$^1$ is C$_{1-6}$ alkyl, and
R$^2$ is phenyl; naphthyl; indanyl; phenyl, naphthyl or indanyl substituted by trihalomethyl, halogen, nitro, nitrile, dioxanyl, dioxolanyl, methyl-dioxanyl, methyl-dioxolanyl, alkyl, cyclopentyl, cyclohexyl, alkenyl, alkynyl, alkoxy, dialkoxymethyl, alkenoxy, alkynoxy, alkylmercapto, alkenylmercapto, alkynylmercapto or dialkylamino, with up to 6 carbon atoms in each alkyl, alkoxy, alkenyl, alkenoxy, alkynyl or alkynoxy group; a radical of the formula

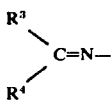

in which
R$^3$ and R$^4$ are each alkyl or alkylthio of 1 to 6 carbon atoms, nitrile or phenyl; or

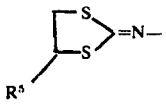

in which
R$^5$ is hydrogen or C$_{1-6}$ alkyl.

Oil  $n_D^{20} = 1.5335$ (10)

melting point
(11)  69°C $n_D^{20} = 1.5370$ (12)

melting point
140°C
(13)

2. A compound according to claim 1, in which R$^1$ is alkyl of 1 to 4 carbon atoms; R$^2$ is phenyl; phenyl substituted by alkyl, alkenyl, alkynyl, alkoxy, alkenoxy, alkynoxy or alkylmercapto each of up to 6 carbon atoms, cyclopentyl, cyclohexyl, halogen, nitro, nitrile, dioxanyl, methyl-dioxanyl, dioxolanyl, methyl-dioxolanyl, dialkylamino with up to 6 carbon atoms in each alkyl moiety, or trihalomethyl; naphthyl; methyl-naphthyl; indanyl; methyl-indanyl; a radical of the formula

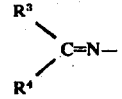

in which
R$^3$ and R$^4$ are each alkyl or thioalkyl of 1 to 6 carbon atoms, nitrile or phenyl;
or

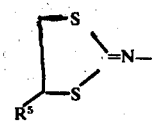

in which
R$^5$ is hydrogen or methyl.

3. The compound according to claim 1 wherein such compound is a mixture of N-methyl-N-methoxycarbonylsulphenyl-m- and -p-isopropylphenylcarbamates of the formula

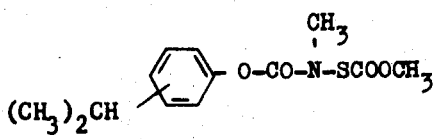

4. The compound according to claim 1 wherein such compound is N-methyl-N-methoxycarbonylsulphenyl- 3,5-dimethyl-4-methylmercapto-phenylcarbamate of the formula

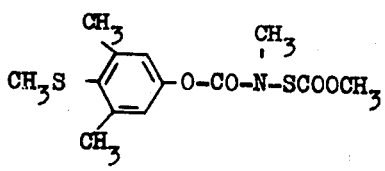

5. The compound according to claim 1 wherein such compound is N-methyl-N-methoxycarbonylsulphenyl-α-methylthioacetaldoximo-carbamate of the formula

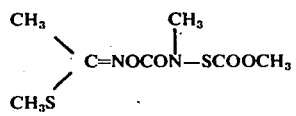

6. The compound according to claim 1 wherein such compound is N-methyl-N-methoxycarbonylsulphenyl-2-2'-dioxolanyl-phenylcarbamate of the formula

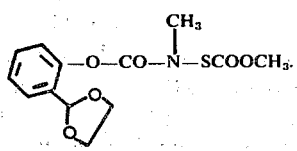

7. The compound according to claim 1 wherein such compound is N-methyl-N-methoxycarbonylsulphenyl-1,3-dithiolan-2-oximo-carbamate of the formula

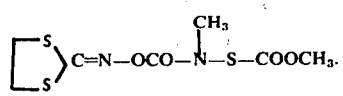

8. An insecticidal, acaricidal, fungicidal, nematocidal or bactericidal composition containing as active ingredient an insecticidally, acaricidally, fungicidally, nematocidally or bactericidally effective amount of a compound according to claim 1 in admixture with a diluent.

9. A method of combating pests selected from the group consisting of insects, acarids, fungi, nematodes and bacteria which comprises applying to the pests or a habitat thereof an insecticidally, acaricidally, fungicidally, nematocidally or bactericidally effective amount of a compound according to claim 1.

10. The method according to claim 9 in which said compound is

N-methyl-N-methoxycarbonylsulphenyl-m- or -p-isopropylphenylcarbamate,

N-methyl-N-methoxycarbonylsulphenyl-3,5-dimethyl-4-methylmercapto-phenylcarbamate, N-methyl-N-methoxycarbonylsulphenyl-α-methylthioacetaldoximo-carbamate, N-methyl-N-methoxycarbonylsulphenyl-2-dioxolanyl-phenylcarbamate, or N-methyl-N-methoxycarbonylsulphenyl-1,3-dithiolan-2-oximo-carbamate.

* * * * *